US00PP10277P

United States Patent [19]

Yates

[11] Patent Number: Plant 10,277

[45] Date of Patent: Mar. 10, 1998

[54] PLUM TREE 'TEAK GOLD'

[75] Inventor: R. A. Yates, deceased, late of Capel, Australia, by Neal William Yates, legal representative

[73] Assignee: TEAK Enterprises, Capel

[21] Appl. No.: 625,024

[22] Filed: Mar. 29, 1996

[51] Int. Cl.[6] ..... A01H 5/00

[52] U.S. Cl. ..... Plt./38.1

[58] Field of Search ..... Plt./38.1

*Primary Examiner*—James R. Feyrer

*Attorney, Agent, or Firm*—Stratton Ballew PLLC

[57] ABSTRACT

The present invention relates to a new and distinct variety of plum tree *Prunus salicina* which was found as a chance seedling. It is characterized by a productive tree of medium vigor which may require some cross pollination. The fruit is semi-freestone, large, conical in shape and has an attractive burgundy colored skin with a slightly aromatic bloom. The underlying flesh is crisp and yellow in color. Eating quality is superb, with a sweet, slightly aromatic flavor and a noticeable absence of acid.

2 Drawing Sheets

ORIGIN OF THE NEW VARIETY

The present new and distinct variety of plum tree, named "Teak Gold," was discovered as a chance seedling in 1978 by Mr. R. A. Yates in his cultivated orchard near Capel River, Western Australia. The parent is unknown, but varieties commonly grown in the area prior to discovery of the new variety include Narrabeen, Wickson, Shiro, and Santa Rosa. The texture and absence of acid in the fruit of the new variety suggest a relationship to Narrabeen.

The new variety was asexually reproduced by top-working at the orchard site and by budding trees in the nursery and shows that all charcteristics of the tree and its fruit run true to the original form and are established and transmitted through succeeding propagations.

SUMMARY OF THE NEW VARIETY

A new and distinct variety of plum tree called "Teak Gold" is described. The variety is characterized by its medium size, compact growth habit and regular and productive bearing of large, firm, attractive, semi-freestone fruit with a noticable absence of acid. The fruit has excellent flavor, aroma and eating quality, and is further characterized by relatively uniform maturity throughout the tree, its ability to hold firm on the tree after maturity (shipping ripe) and its ability to ship and store well under cold room regime and on the grocer's shelf.

PHOTOGRAPHS OF THE NEW VARIETY

The accompanying color photographs show typical specimens of the foliage and fruit of the new plum variety.

DESCRIPTION OF THE NEW VARIETY

Tree Description

Growth Habit

Figure 1:
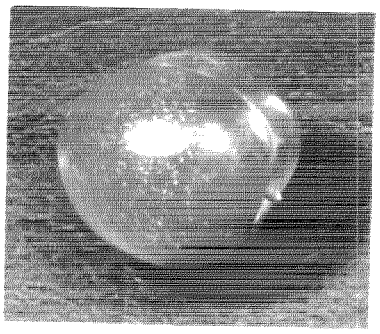
FIGS. 1 and 2 show the fruits with stems attached. The photographs were taken shortly after the fruit was picked at maturity (firm ripe) and the colors are as nearly true as is reasonably possible to a color representation of this type.
Figure 2:
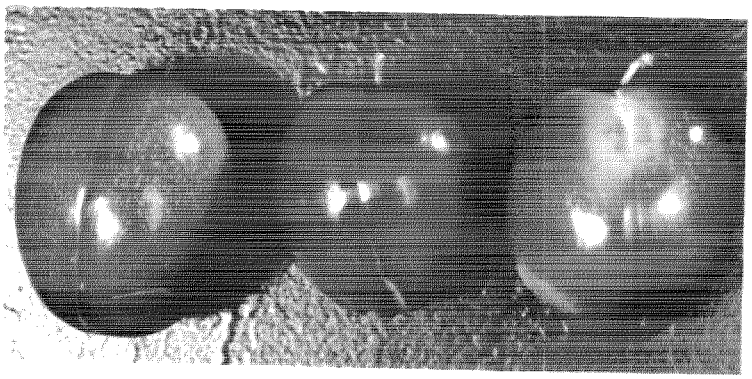
Figure 3:
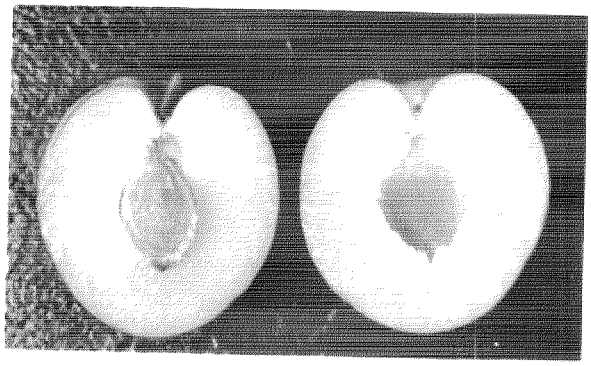
FIG. 3 shows a fruit sectioned and laid open with the stone and stem left in place in one section and the stone removed to expose the pit cavity in the other section.
Figure 4:
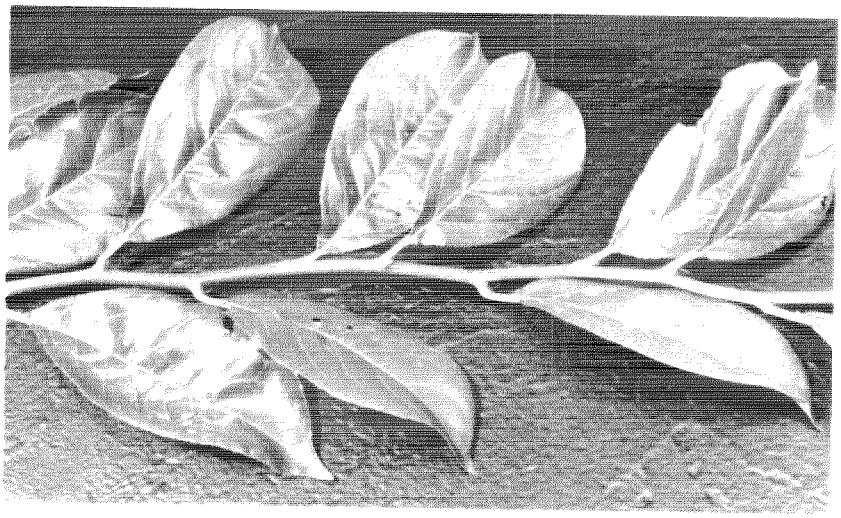
FIGS. 4 and 5 show representative twigs, spurs and leaves of the new variety.
Figure 5:
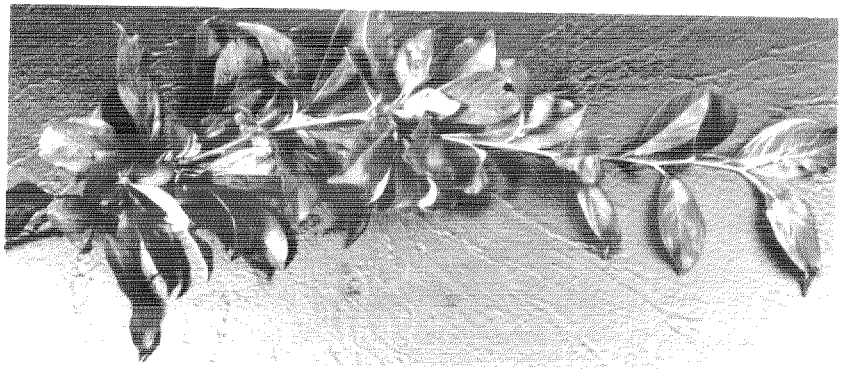

The vegetative habit of Teak Gold is best described as a compact tree of medium vigor and size. The variety grows vigorously for the first two years before beginning crop productions.

Fruit buds develop readily on upright one year old wood. An initial production assessment confirms that Teak Gold has a moderate chilling requirement and may be suitable for commercial production in world fruit production regions receiving as little as five hundred (500) hours of winter chilling, below 7° C.

Fruit

The fruit is large, conical in shape with an attractive burgundy colored surface, with a slightly aromatic bloom. The underlying flesh is deep yellow. Picked at the correct maturity indices, the eating quality is superb. Its flesh is crisp and fresh with a noticeable absence of acid and has a sweet, slightly aromatic flavor. The fruit matures slowly and will remain on the tree in a firm ripe condition for up to one week without losing eating quality. Table 1 illustrates the favorable comparison of harvest maturity standards of Teak Gold to known varieties.

TABLE 1

COMPARATIVE HARVEST MATURITY STANDARDS

| | Firmness (kg 11.1 mm plunger) | Total Soluble Solids (TSS %) |
|---|---|---|
| TEAK GOLD | 5.5–6.5 | >18 |
| LARODA | 6.0–7.5 | 13.0–16.0 |
| FRIAR | 8.0–9.0 | 13.0–14.0 |
| QUEEN ANN | 6.0–6.5 | 14.5–16.5 |
| NARRABEEN | 6.0–7.5 | 13.0–14.5 |

An initial research program has found that Teak Gold fruits, if picked at the optimum maturity, have a storage life of about one month, with a further retail shelf life of seven days. This compares favorably with other popular varieties of plum.

Production

Rootstock

Teak Gold has been grown successfully on a range of rootstocks including plum, (Myrobalan & Mariana) and peach (Fort Valley & Nemaguard). Teak old trees on plum rootstocks are more suited to heavy clay loam soils or where the soil is poorly drained. Teak Gold trees on peach rootstocks do not do well when planted in poorly drained, heavier clay type soils.

Teak Gold trees grown on peach rootstocks are smaller than those grown on either Myrobalan or Mariana plum rootstocks.

Pollination

Experience indicates that Teak Gold may be partially self pollinating. Commercial crops have been harvested from plantings of Teak Gold grown without any source of cross pollinating plum varieties. However, as a precaution, it is recommended that pollinators be included in plantings of Teak Gold. The following Japanese plum varieties appear to be suitable pollinators: Santa Rosa, Laroda, Friar and Kelsey.

Nutrition

A green purpose fertilizer program for stonefruit production is suitable for Teak Gold. Excess application of nitrogenous fertilizer will adversely affect fruit quality.

Standard horticultural practice which provides the tree with liberal quantitites of the essential balanced elements during the establishment phase of the orchard is recommended. Once the trees begin producing, nutrition must be managed to ensure the production of fruit quality with sufficient tree vigor for adequate replacement of fruiting wood.

Teak Gold does appear to run out of vigor with age and under heavy cropping. Careful management of nutrition and pruning will extend the productive life of the tree.

Irrigation

Teak Gold will size its fruit steadily throughout the growing season. The new plum variety does not appear to respond to heavy irrigation in the last month leading up to harvest as observed with many other Japanese plum varieties. Maintenance of adequate, steady levels of moisture throughout the growing season is recommended. Restricted irrigation early in the growing season followed by heavy watering in the last four (4) to six (6) weeks prior to harvest may cause fruit cracking.

Cropping

Teak Gold is a very fruitful variety and will form fruit buds and set fruit on one year old wood.

The first commercial crop can be expected in the third year, with production rising quickly. Yields of 30–40 tons per hectare have been achieved in the fifth leaf at twelve hundred and fifty (1250) trees per hectare with production expected to level out at around 45–50 tons per hectare in productive, well managed orchards.

Teak Gold has the ability to produce heavy crops of medium sized fruit (48–50 mm) with limited hand thinning on trees with a full set. Thinning would involve breaking the fruit clusters down to single fruits.

For larger fruit size (60 mm+) fruit should be spaced at 75–100 mm.

The best results are achieved if thinning is done early, preferably around stone hardening.

The new plum variety normally requires two picks. The fruit may show skin browning if picked during extreme heat. It is important that the fruit is harvested at its optimum maturity, pre-cooled quickly, stored at 0° C. and maintained under a cool chain regime from the orchard to the consumer.

Production Systems

Teak Gold can be grown on a number of training systems including free standing pillar or central leader, palmette and Tatura Trellis.

Tree densities may vary in range from 800–2500 trees per hectare.

The recommended tree spacing for Teak Gold for different training systems are:

Palmette: 4 m×2 m; 1250 trees/ha.
Pillar: 4 m×1–1.5 m; 1700–2500 trees/ha.
Tatura Trellis: 5 m×1 m; 2000 trees/ha.

These training systems aim to achieve maximum tree canopy area per hectare as quickly as possible with the objective of harvesting a commercial crop in the third year.

DESCRIPTION OF THE VARIETY

All color designations indicated are from the Munsell Color Cascade Chart, or as described by ordinary dictionary significance.

1. Tree:
   *Size.*—Medium.
   *Vigor.*—Medium.
   *Form.*—Upright.
   *Density.*—Very dense.
   *Bearing.*—Regular.
   *Productivity.*—Very Productive.
2. Trunk:
   *Size.*—Medium to large.
   *Texture.*—Medium shaggy.
   *Color.*—Brown to grayish brown (24-14).
3. Branches:
   *Size.*—Medium.
   *Texture.*—Medium rough.
   *Lenticels.*—Medium in number, large size.
   *Color.*—Brown (26-12).
4. Leaves:
   *Size.*—Medium; Average length 110 mm; Average width 52 mm.
   *Margin.*—Very finely serrated.
   *Form.*—Oblanceolate — pointed.
   *Glands.*—Very few, very small, globose, number varies from mostly 0 to 2. Positioned on upper portion of petiole and on the base of the leaf blade, usually alternate.
   *Color.*—Upper surface — green to dark green (22-11). Lower surface dark green (22-12).
5. Flower buds:
   *Size.*—Medium.
   *Length.*—Medium.
   *Form.*—Plump.
6. Flowers:
   *Size.*—Medium.
   *Pollen.*—Present.
   *Color.*—White.
   *Blooming period.*—Mar. 16, 1995 to Apr. 1, 1995. Varies with climatic conditions.
7. Fruit:
   *Maturity when described.*—Firm ripe.
   *Date of first picking.*—Aug. 28, 1995.

*Date of last picking.*—Sep. 6, 1995.
*Size.*—Large, uniform, average diameter axially 67 mm; Average transversely in suture plane 64 mm.
*Suture.*—Shallow — extends from base to apex.
*Ventral surface.*—Round, smooth.
*Form.*—Conical, slightly elongated.
*Cavity.*—Rounded, average length 15 mm, average breadth 15 mm.
*Base.*—Slightly retuse.
*Apex.*—Usually pistil point; Varies from rounded to pistil point.
*Stem.*—Average length 10 mm.

8. Flesh;
*Texture.*—Finn.
*Juice.*—Juicy, but no free-flowing juice.
*Ripens.*—Some unevenness;Two picks best.
*Fibers.*—Small, tender.
*Flavor.*—Excellent — Low acid, sweet, slightly aromatic.
*Eating quality.*—Excellent.
*Aroma.*—Slight.
*Color.*—Light yellow (6-9), even throughout.
*Pit cavity.*—Brownish yellow (27-11).

9. Skin:
*Thickness.*—Medium.
*Texture.*—Medium, tenacious to fleshy.
*Tendency to crack.*—None.
*Bloom.*—Slight.
*Down.*—Wanting.
*Color.*—Burgundy Red (42-13) Yellow Base (26-8).

10. Stone:
*Type.*—Mostly freestone.
*Size.*—Medium. Average length 30 mm; Average width 19 mm; Average thickness 14 mm.
*Form.*—Ovate.
*Apex.*—Slightly acute.
*Base.*—Rounded.
*Sides.*—Nearly equal.
*Surface.*—Slightly pitted; Slight grooves at apex end.
*Tendency to split.*—Minimal (under excessive tree vigour a small proportion of the crop will exibit cracked stones).
*Color.*—Light brown (27-10).
*Use.*—Dessert.
*Market.*—Local and long distance.
*Storage quality.*—Good.
*Shipping quality.*—Good.

The present new plum tree, its foliage, flowers and fruit herein described may vary in slight detail due to the climate, soil conditions and cultural practices under which the variety may be grown. The present description is that of the variety grown under the ecological conditions prevailing near Parker, Wash. U.S.A.

What is claimed is:

1. A new and distinct variety of plum tree, substantially as illustrated and described, characterized by its medium size, compact growth habit and being a regular and productive bearer of large, firm, attractive, semi-freestone fruit with excellent flavor, aroma and eating quality. The fruit is further characterized by relatively uniform maturity throughout the tree, its ability to hold firm on the tree after maturity (shipping ripe) and its ability to ship and store well under cold room regime and on the grocer's shelf.

* * * * *